United States Patent [19]
Riedlinger

[11] Patent Number: 5,947,916
[45] Date of Patent: Sep. 7, 1999

[54] FASTENING ARRANGEMENT FOR A LIMB SUPPORT DEVICE

[75] Inventor: John Riedlinger, Lake Villa, Ill.

[73] Assignee: Plasco, Inc., Gurnee, Ill.

[21] Appl. No.: 08/870,934

[22] Filed: Jun. 6, 1997

[51] Int. Cl.$^6$ ....................................................... A61F 5/00
[52] U.S. Cl. ................................ 602/5; 602/61; 24/114.5
[58] Field of Search ................................... 24/114.5, 713; 602/5, 12, 20, 23, 61; 128/869–871, 874–876

[56] References Cited

U.S. PATENT DOCUMENTS

| | | |
|---|---|---|
| 1,373,349 | 3/1921 | Peardon . |
| 1,848,318 | 3/1932 | Ciampi . |
| 2,637,084 | 5/1953 | Lorentzen . |
| 3,279,015 | 10/1966 | Henning . |
| 4,612,925 | 9/1986 | Bender . |
| 4,656,679 | 4/1987 | James . |
| 4,672,507 | 6/1987 | Huttner ..................................... 485/55 |
| 4,801,136 | 1/1989 | Askins ..................................... 482/55 |

*Primary Examiner*—Linda C. M. Dvorak
*Attorney, Agent, or Firm*—Jerome Goldberg

[57] ABSTRACT

A fastening arrangement for a limb support device includes a formable jacket having a top side and a bottom side. An injured limb or body part is positioned on the bottom side. The jacket is formed to the desired shape for supporting and protecting the limb. A belt holder having an opening is rigidly secured to the top side. A belt passes through the opening of the holder. A stud is pivotally attached to the belt and extends outward from the upper side of the belt. The stud abuts the holder to anchor the stud against the holder and prevent movement of the stud and belt through the opening of the holder when the belt is pulled in one direction. This maintains a fixed length of the belt from one end of the belt to the anchored stud. The ends of the belt are connected together after the stud is anchored. Belt length adjustment means is provided to vary the remaining length of the belt (other than the fixed length) from the anchored stud to the opposite end of the belt, for securely fastening the jacket to the injured limb. The stud is movable to lie substantially flat on said belt to permit movement of the belt and stud through the holder opening. To remove the limb support device, the ends of the belts are disconnected. To reattach the limb support device, the belts ends are reconnected and no adjustments of the belt lengths are required.

18 Claims, 4 Drawing Sheets

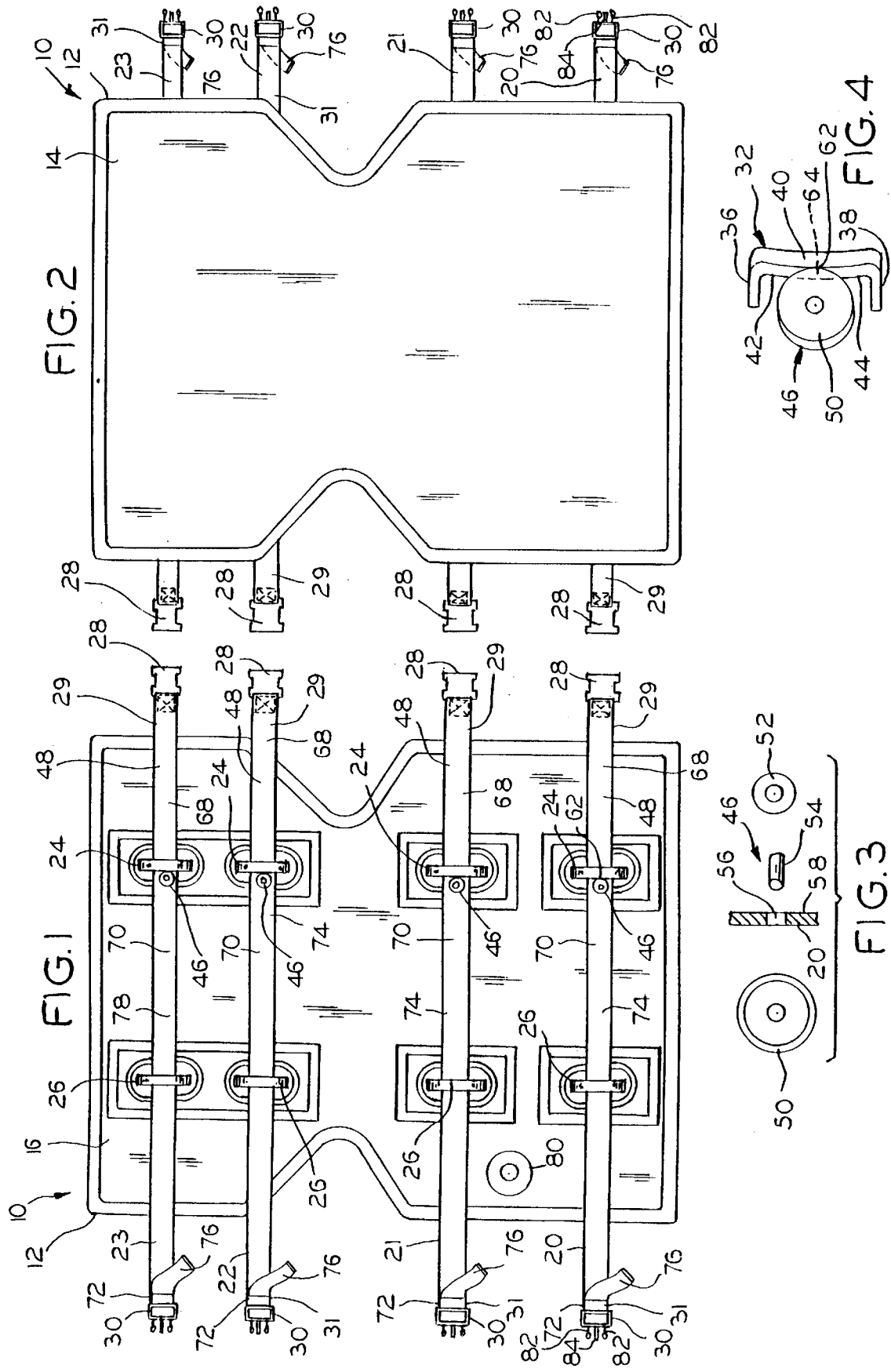

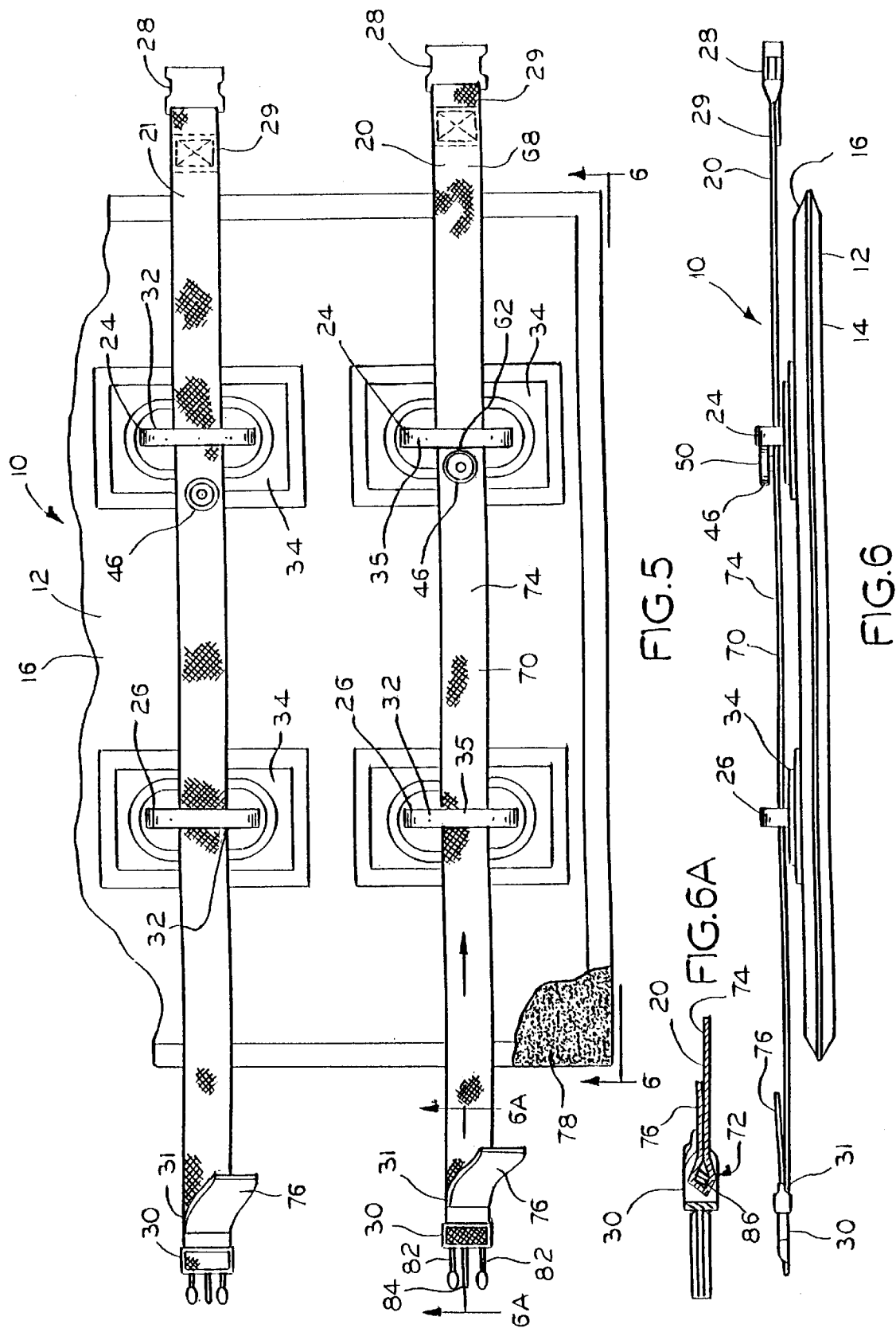

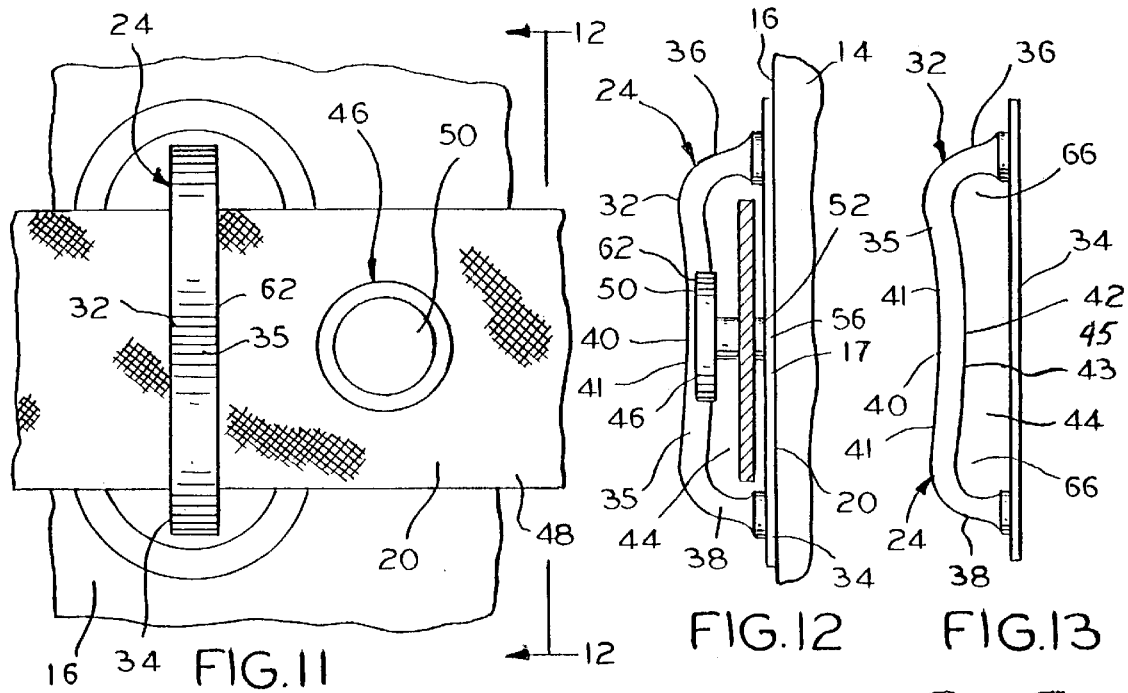
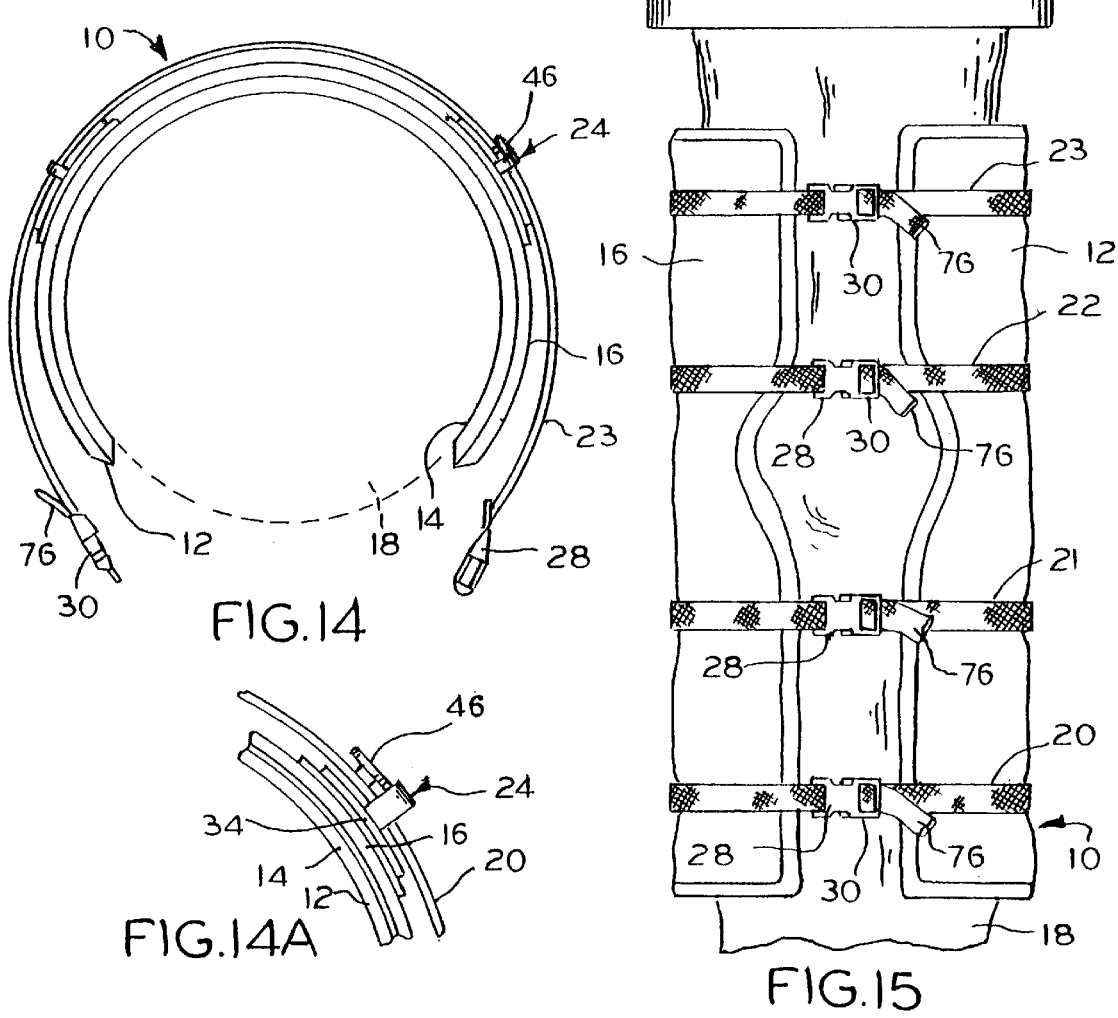

FASTENING ARRANGEMENT FOR A LIMB SUPPORT DEVICE

BACKGROUND OF INVENTION

The invention relates generally to a fastening arrangement for a splint or limb support; and more particularly relates to an adjustable fastening arrangement for a formable limb support. Still more particularly the invention relates to a fastening arrangement for a formable limb support having a mass of movable beads or pellets confined inside a bag or jacket for forming the limb support and the formed shape of the bag becomes rigid upon evacuating air inside the bag to create a vacuum.

Many fastening means have been used in the past for attempting to immovably secure an injured limb in a splint arrangement. Conventional belts have been frequently used, but in a short time, the belts would slip from side to side and loosen, causing movement of the injured limb and thereby creating the possibility of further damage or injury to the limb.

In recent times "Velcro" type strips or belts have commonly been used as attaching means for limb supports, such as the formable limb supports referred to above. Prior such belts included fastening strips at one end of the belt having a plurality of loops to function as the female complementary part of "Velcro" type connectors for connecting with fastening strips at the opposite end of the belt including a plurality of hooks to function as the male complementary part of the "Velcro" type connectors. These Velcro fasteners in a short time tended to loosen or disattach and thereby weaken the support and effectiveness of the splint.

Furthermore, the Velcro fasteners were generally permanently attached to the limb support device and were not removable. Hence, the Velcro fasteners could not be readily cleaned or washed to remove contaminants and impurities, such as dirt, blood stains etc.

Moreover, after disconnecting the prior belts, appreciable time and effort were required to securely reconnect the belts around the limb supports.

The subject invention overcomes the problems with the prior splint fasteners by providing a limb support having adjustable means for easily securing the limb support on or around the injured limb.

It is therefore a primary object of the invention to provide an attaching arrangement which securely fastens a limb support on or around the injured limb or body part.

Another primary object is to provide fastening means for a limb support which may be quickly and securely attached to the limb support protecting the injured limb.

Another object is to provide a fastening means for a formable limb support that is easily adapted to be used on various parts of the body and is suitable for use with various sized persons.

Another object is to provide a fastening means that requires initial adjustments for securing the limb support to the injured limb; and after disconnection of the fastening means for whatever reason, the fastening means may be easily reconnected without further adjustment.

Still another primary object is to provide a limb support device having a detachable fastening belt which could be readily cleaned or washed to remove contaminants and impurities, such as dirt, blood stains etc., prior to a subsequent use.

SUMMARY OF INVENTION

In accordance with one embodiment of the invention, a limb support device is provided for quickly and securely fastening the limb support on or around an injured limb or body part. The limb support includes a jacket having a bottom side for supporting the injured limb and a top side. At least one belt holder having an opening is secured to the top side of the jacket. A fastening belt extends through the opening of the belt holder and includes a first end for connecting to a second end. A pivotal stud is secured to the belt between the first and second ends, and projects outward from the upper side of the belt. The stud abuts the belt holder to anchor thereto and divide the belt into a first belt portion having a fixed length extending from the point of anchor, through the holder and to the first end; and a second belt portion extending from the point of anchor to said second end. Belt adjustment means varies the length of the second belt portion for securely fastening the belt around the jacket supporting the injured limb.

Therefore, the belt is positioned through the belt holder. The belt is pulled in one direction to cause the stud to abut and anchor to the belt holder to prevent any belt movement in the one direction. The belt ends are connected together, and belt length adjustment means is provided for varying the length of the second portion of the belt to set the desired belt length, after the stud is anchored.

The stud is positioned substantially flat on said belt to enable the stud and belt to pass through the opening of the belt holder. The stud may be pivoted to an angled position with respect to the belt when the stud abuts the belt holder.

The belt holder includes a handle having an upper bar formed to a pair of spaced apart legs which are attached to the top side of the jacket. The upper surface of the bar has a concave curvature and the stud contacting the concave curvature when abutting the belt holder for preventing movement of the belt. The lower surface of the upper bar includes a convex hump which prevents movement of the stud through the opening of the belt holder except when the stud lies substantially flat on the upper surface of the fastening belt.

Therefore, a primary feature of the invention is to provide a limb support device including a fastening belt extending through an opening in a belt holder, and having a pivotal stud for preventing movement of the belt through the opening when the stud abuts the belt holder.

Another primary feature is to provide a limb support device having a removable fastening belt to afford easy means for cleaning and washing the fastening belt.

Another feature is to provide a belt having a pivotal stud including a button normally spaced above the upper side of the belt, and the inner or lower surface of the button abutting a belt holder to prevent movement of the belt and stud through the belt holder.

Another feature is to provide a belt having a pivotal stud that may be positioned substantially flat on the belt for passing through a a belt holder.

Still another feature is to provide a fastening belt divided into a first portion having a fixed length and a second portion having a variable length, and the belt portions are connected together.

Still another feature is to provide a removable and adjustable fastening belt for a limb support device to enable the belt to be washed and disinfected.

BRIEF DESCRIPTION OF THE DRAWINGS

Referring to the drawings in which the same characters of reference are employed to indicate corresponding similar parts throughout the several figures of the drawings.

FIG. 1 is a top view of a limb support device, embodying the principles of the invention, and illustrating a plurality of spaced apart belts, each having a stud for anchoring against a belt holder secured to the limb support;

FIG. 2 is a bottom view of the limb support where an injured limb is placed;

FIG. 3 is an exploded and fragmentary view of the anchor stud and its associated parts;

FIG. 4 is a perspective view of the stud anchored to the handle of the belt holder;

FIG. 5 is a fragmentary top view of the limb support device and illustrating a pair of spaced apart belts having studs for anchoring against the corresponding belt holders of the limb support;

FIG. 6 is a side view of the limb support and belt fasteners of FIG. 5, taken on the plane of the line 6—6 in FIG. 5, and viewed in the direction indicated;

FIG. 6A is a fragmentary sectional view, taken on the plane of the line 6A—6A in FIG. 5, viewed in the direction indicated, and illustrating the adjustment means for varying the belt length;

FIG. 11 is a fragmentary top view showing the stud spaced from the belt holder;

FIG. 12 is a rear view of FIG. 11, taken on the plane of the line 12—12 in FIG. 11, and viewed in the direction indicated;

FIG. 13 is a rear view of the belt holder;

FIG. 14 is an end view of the limb support device wrapped around the injured body part (shown in phantom) prior to securing the limb support device with the belt fasteners;

FIG. 14A is a fragmentary and enlarged end view of the limb support device of FIG. 14 to show the stud anchored against the belt holder; and FIG. 15 illustrates the limb support device fastened to the injured limb shown in phantom.

DESCRIPTION OF THE PREFERRED EMBODIMENT

Figure 7:
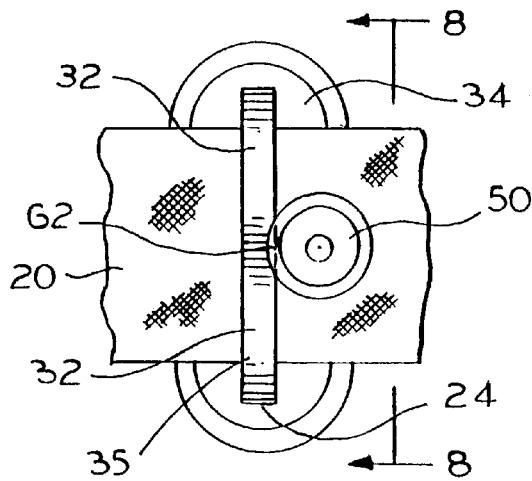
FIG. 7 is a fragmentary top view showing the stud of a belt anchored against a belt holder.
Figure 8:
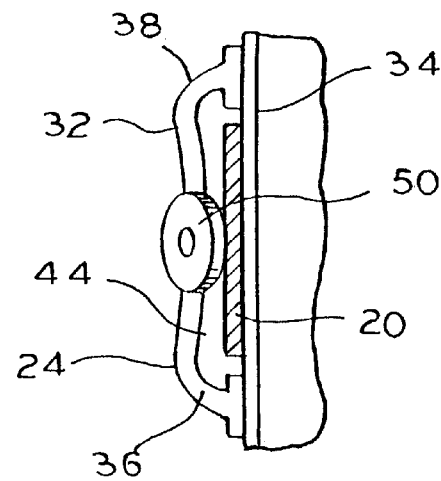
FIG. 8 is a fragmentary rear view of the stud anchored to a belt holder, taken on the plane of the line 8—8 in FIG. 7, and viewed in the direction indicated.
Figure 9:
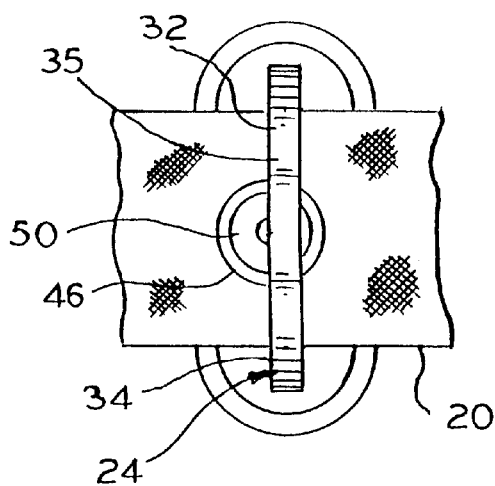
FIG. 9 is a fragmentary top view of the stud passing between the handle and the base of the belt holder.

Referring now more particularly to the several figures of the drawings, the reference numeral 10 indicates generally a limb support device comprising a compressible and pliable jacket 12. The jacket 12 includes a limb support side 14 (FIG. 1) and a belt support side 16 (FIG. 2). The injured limb or body part 18 (FIG. 15) is placed on the limb support side 14. Belts 20, 21, 22 and 23 secure the support device 10 to the injured limb 18.

As shown in FIG. 1, a pair of belt holders 24 and 26 are associated with each of the belts 20, 21, 22, and 23. The belt holders 24 and 26 extend outward from the belt support side 16 of jacket 12. More than two belt holders may be used in conjunction with a single belt to provide greater adjustability for fastening the limb support device.

Each belt 20, 21, 22 and 23 includes a female connector 28 at one end 29 and a complementary mating male connector 30 at the opposite end 31 of the corresponding belt. The belts and belt holders in the described embodiment are equivalent to each other, and any description pertaining to one belt and associated belt holders will apply to the other belts and belt holders.

Turning now more specifically to FIG. 13, it will be seen that the belt holder 24 (or 26) includes a handle 32 secured to a base member 34. The handle 32 comprises an outer bar 35 integrally formed to spaced apart opposed legs 36, 38. The outer bar 35 includes a depression 40 at the substantial center thereof which forms a concave surface 41. This causes the bar 35 to protrude inward on the inside of the belt holder to form a hump 42 having a convex surface 43.

The belt holder 24 includes an opening 44 defined by the upper bar 35, the legs 36, 38 and the base member 34. The belt 20 (or belts 21, 22, and 23) passes through the opening 44 of the belt holder. As may be seen, the most restrictive area in the opening 44 is the space 45 between the hump 42 and the base 34 (FIG. 13).

Each belt 20, 21, 22 and 23 includes a stud 46 positioned at a fixed point on the belt and extending outward from the upper side 48 of the corresponding belt. The stud 46 includes a button 50, a foot 52 and a pin 54 (FIG. 3). The pin 54 extends through an aperture 56 formed in the corresponding belt for attachment to the button 50 and the foot 52. The stud 46 is pivotal in any direction at the point of attachment on the belt. Normally, the button 50 is spaced above the upper side 48 of the belt and the foot 52 loosely contacts the lower side 58 of the belt. In the illustrative embodiment, the stud 46 is attached to the belts between the female and male connectors 28 and 30 but is closer to the female connector 28 (FIGS. 1 and 5).

When, for example, the belt 20 is moved through the corresponding belt holders 24, 26 by pulling the female end 28 laterally outward, the stud 46 moves toward belt holder 24 as may be seen in FIG. 5. The button 50 then contacts the rear edge 62 (with respect to the female belt end 28) of the upper bar 35 of the handle 32 of belt holder 24, so that the rear edge 62 of the upper bar 35 abuts the bottom surface 64 of the button 50 to anchor the stud 46 (or button 50) against the belt holder 24 (FIGS. 1 and 5).

Figure 10:
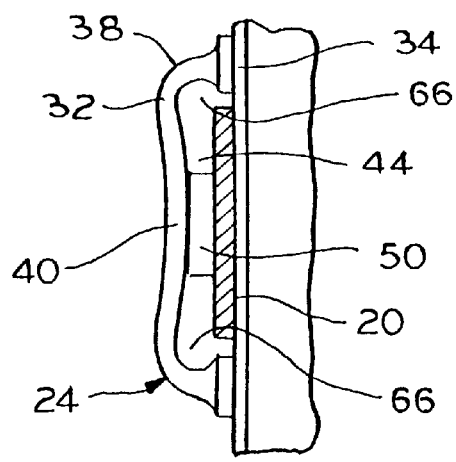
FIG. 10 is a fragmentary rear view of the stud passing between the handle and the base of the belt holder (rear view of FIG. 9)

To move the stud 46 through the holder 24, the button 50 is positioned substantially flat on the belt 20 and the belt and the stud 46 are pulled through the opening 44. The button 50 may be pulled through the opening 44 at the opposite sides 66 of the hump 42. The button 50 may also be pulled through opening 44 in the space 45 between the hump 42 and the base member 34 as shown in FIG. 10, provided that the button 50 is set flat on the belt prior to pulling the belt and stud 46 through the space 45 (FIG. 13).

Referring now more particularly to FIGS. 1 and 5 of the drawings, it will be seen that the female connectors 28 at ends 29 of the belts 20, 21, 22, and 23 are pulled laterally outward until the corresponding studs 46 abut the rear edges 62 of the upper bars 35 of handles 32 of the belt holders 24. Further pulling of the belt ends 29 cause the studs 46 to more tightly engage or abut the belt holders 24 to anchor thereto and provide a belt portion 68 having a fixed length between the anchored stud 46 and the female connector 28 at the end 29 of the corresponding belt. The length of the remaining belt portion 70 is adjustable.

The male connector 30 includes a belt length adjustment means 72 for dividing the remaining belt portion 70 into an operable belt section 74, between the stud 46 and the male connector 30 for wrapping around the jacket and the injured limb; and a non-operable belt section 76 extending out from the male connector 30. To increase the length of the operable belt section 74, the length of the non-operable belt section 76 is decreased and visa versa. The belt length adjustment means 72 may be a conventional and commonly used means for varing belt length.

Turning now to FIG. 15, the setting for each of the female connectors 28 of the fastening belts is initially set and lie on the same vertical plane. For this to occur, the stud 46 of each belt is anchored to the same corresponding belt holder 24, such as each stud 46 is anchored to belt holder 24 when the corresponding female connector 28 is pulled laterally outward.

The ends 31 of the fastening belts 20, 21, 22, and 23 having the male connectors 30 are pulled around the jacket 12 and limb 18 in a counter clockwise direction and toward the end 29 having the female connector 28.

The male connectors 30 are mated with the female connectors 28. Then, the length for the operable belt length 74 is adjusted with the belt length adjustment means 72 to provide the desired tightness and support for the injured limb. It may be advantageous to adjust the length of the operable belt section 74 prior to the connection of the female and male connectors 28 and 30; and make another or fine adjustment after connecting the female and male connectors 28 and 30.

To unwrap or disconnect the belts for removing the support device 10 to treat a wound or change a bandage or for whatever other reason, it is just required to disconnect the male connectors 30 from the female connectors 28 and open the jacket 12 to access the injured limb. To reposition the support device back on the limb 18, it is simply necessary to reconnect the male connectors 30 to the female connectors 28. No adjustments of the belt lengths are required after the initial adjustments of the belt lengths have been made.

Referring now to FIG. 5, it will be seen that the jacket 12 is cut away to show the mass 78 of movable beads, pellets or sand confined inside the jacket 12. The limb support device 10 is formed to the shape of the injured limb or body part to be supported. Then a vacuum is created in the jacket 12 via valve 80 (FIG. 1). This causes the pellets to harden together to form the desired protective and rigid mold for the injured limb or body part. Then the belts 20, 21, 22 and 23 are positioned and adjusted as aforesaid to securely fasten the belts around the jacket 12 and the injured limb.

Thus, the male ends 30 of the belts 20, 21, 22 and 23 are pulled laterally outward so that the stud 46 of each belt 20, 21, 22 and 23 is anchored against the selected belt holder 24, to provide the desired length for the fixed belt portion 68. The remaining belt portion 70 is wrapped around the rigidly formed jacket 12. The length of the remaining belt portion 70 is adjusted with the belt adjustment means 72 to provide the desired belt tension for fastening the formed jacket 12 around the injured limb when the belt connectors 28 and 30 are connected together after the stud 46 is anchored to the belt holder 24. When the customized limb support device 10 is no longer needed, air is introduced into the jacket via valve 80, causing the jacket to be compressible and pliable again and ready for a future use.

The female and male connectors 28, 30 may be of the conventional type. For example, the male connector 30 may comprise a pair of opposed resilient prongs 82 spaced form a center pin 84. The prongs 82 bend inward toward the pin 84 when the male connector 30 is initially inserted into the female connector 28 and thereafter resiliently moves outward away from the pin when to lock inside the female connector 28 when the connection is completed. The center pin 84 rides on a track inside the female connector 28.

The belt adjustment means 72 is illustrated in FIG. 6A. The belt 20 passes over a support member 86 to the outside. If the non-usable (or non-operable) belt section 76 is pulled outward the length of belt section 76 is increased and the length of the operable or usable belt section 74 is decreased. However, if the belt section 74 or 76 is pulled in the opposite or inward direction, the opposite occurs, and the length of the operable belt section 74 is increased and the length of the non-operable belt section 76 is decreased.

In the illustrated embodiment, the stud 46 may be anchored to either belt holder 24 or 26. However, the distance between the belt holders 24 and 26 is less than the distance between the stud 46 and the female connector 28. Similarly, the distance between the belt holders 24 and 26 is less than the distance between the stud 46 and the male connector 30. The distance relationships prevent collision of the connectors with belt holder 26 when the stud 46 is anchored to belt holder 24 or 26.

Since the stud 46 is pivotal in any direction (through a range of 360 degrees), the same stud 46 may be used to anchor against either side of the belt holders 24 or 26, when fastening the jacket 12 around the injured limb 18.

The fastening arrangement described herein is also suitable for jackets covering injured limbs which do not utilize a mass of pellets 78, to become rigid upon creating a vacuum, It is also within the contemplation of the invention that the fastening arrangement described herein may find uses in addition to those discussed in this specification.

Various modifications of the invention of a fastening arrangement for a limb support device described and illustrated herein, are within the spirit and scope of the invention, the scope of which is limited solely and defined by the appended claims.

I claim:

1. A device for supporting an injured limb comprising:
   a jacket having a bottom side for placing said limb and a top side;
   at least one belt holder secured to the top side of the jacket, said holder including an opening;
   a belt having an upper side and a lower side, said belt including a first end and a second end, said belt passing through said holder opening;
   a stud secured to said belt between said ends, said stud extending outward from the upper side of the belt for abutting said holder to prevent movement of the belt through said opening, distance of the stud from the holder varying as the belt passes through said holder opening; and
   connecting means for connecting said ends together.

2. The limb support device of claim 1 includes:
   a female connector attached to one end of the belt; and
   a male connector attached to the opposite end of the belt, said female and male connectors being mated together after said stud abuts said belt holder.

3. The limb support device of claim 1, wherein said belt includes:
   a first portion; and
   a second portion, said second portion passing through said holder opening, said first portion extending from one of said ends to said stud, said second portion extending from said stud to the other of said ends.

4. The limb support device of claim 3, wherein said first portion is a fixed length and said device further including:

adjustment means for varying the length of said second portion, for securing the device to the limb.

5. The limb support device of claim 4, includes:

a second holder having a second opening, said second holder being spaced from the first holder, said stud contacting said second holder to anchor thereto and prevent movement of the belt through said second opening, said first end being connected to said second end when the stud is anchored to the second belt holder.

6. The limb support device of claim 4, wherein:

the distance between the first and second holders is less than the distance between said stud and said one of said ends.

7. The limb support device of claim 4 wherein:

said second portion of the belt includes an operative section for wrapping around the jacket and a non-operative section, said belt adjustment means varying the length of said operative section of the belt and the length of said non-operative section of the belt.

8. The limb support device of claim 7, wherein said adjustment means increases the length of the operative section of the second portion of the belt and simultaneously decreases the length of the non-operative section of the belt and visa versa.

9. The limb support device of claim 1, wherein said stud is pivotally attached to said belt.

10. the limb support device of claim 1, wherein said stud is pivotally movable through a range of 360 degrees.

11. A device for supporting an injured limb comprising:

a jacket having a bottom side for placing said injured limb and a top side;

a substantially inverted "U" shaped belt holder having an upper bar formed to spaced apart legs, said legs being secured to the top side of the jacket, said bar and legs defining an opening;

a belt having an upper side and a lower side, said belt including a first end and a second end, said belt passing through said holder opening;

a stud secured to said belt between said ends, said stud extending outward from the upper side of the belt for abutting said bar to prevent movement of the belt through said opening; and connecting means for connecting said ends together.

12. The limb support device of claim 11, wherein said upper bar includes a hump to restrain movement of the stud through said opening.

13. The limb support device of claim 12, wherein said belt and said stud are movable through said opening and past said hump when said stud is substantially flat with respect to said top side of the belt.

14. The limb support device of claim 11, wherein said belt and said stud are movable through said opening when the stud is substantially flat with respect to the upper side of the belt.

15. The limb support device of claim 1, wherein an aperture is formed in said belt and said stud includes:

a button;

a foot; and a pin, said pin extending through said aperture for attachment to said button and said foot, said button abutting said holder.

16. The limb support device of claim 15, wherein said button is normally spaced above the upper side of the belt, and said foot is loosely contacting said bottom side of the belt.

17. The limb support device of claim 11, wherein said upper bar includes a top surface having a depression formed therein, said stud being positioned adjacent said depression when abutting the upper bar of the holder.

18. The limb support device of claim 11, wherein the contact of the holder with the stud causes the stud to incline from the top side of the belt to the point of contact of the stud with the upper bar of the belt holder.

* * * * *